(12) United States Patent
Craine et al.

(10) Patent No.: US 6,427,022 B1
(45) Date of Patent: Jul. 30, 2002

(54) IMAGE COMPARATOR SYSTEM AND METHOD FOR DETECTING CHANGES IN SKIN LESIONS

(75) Inventors: Eric R. Craine, Tuscon, AZ (US); Brian L. Craine, Fairfax, CA (US)

(73) Assignee: Western Research Company, Inc., Tucson, AZ (US)

( * ) Notice: Subject to any disclaimer, the term of this patent is extended or adjusted under 35 U.S.C. 154(b) by 0 days.

(21) Appl. No.: 09/189,482

(22) Filed: Nov. 10, 1998

(51) Int. Cl.[7] .................................................. G06K 9/00
(52) U.S. Cl. ........................................ 382/128; 128/922
(58) Field of Search ................................. 382/128, 129, 382/130, 131, 132, 112; 358/473; 424/646; 700/57

(56) References Cited

U.S. PATENT DOCUMENTS

| | | | | |
|---|---|---|---|---|
| 4,404,590 A | | 9/1983 | Mayer et al. ................ 358/106 |
| 4,437,117 A | * | 3/1984 | Haendle et al. ................ 378/98 |
| 4,602,280 A | | 7/1986 | Maloomian ................... 358/93 |
| 4,670,781 A | | 6/1987 | Aubert et al. ................. 358/93 |
| 4,747,146 A | * | 5/1988 | Nishikawa et al. ............ 382/1 |
| 4,905,702 A | | 3/1990 | Foss ........................... 128/665 |
| 4,922,909 A | | 5/1990 | Little et al. .................. 128/630 |
| 4,996,994 A | | 3/1991 | Steinhauer et al. .......... 128/774 |
| 5,016,173 A | * | 5/1991 | Kenet et al. ............ 364/413.13 |
| 5,018,531 A | | 5/1991 | Hartman ...................... 128/774 |
| 5,099,859 A | | 3/1992 | Bell ............................ 128/781 |
| 5,146,923 A | | 9/1992 | Dhawan ....................... 128/633 |
| 5,249,581 A | | 10/1993 | Horbal et al. ................ 128/664 |
| 5,291,889 A | | 3/1994 | Kenet et al. ................. 128/653 |
| 5,681,593 A | * | 10/1997 | Smith et al. ................. 424/646 |
| 6,005,681 A | * | 12/1999 | Pollard ....................... 358/473 |
| 6,049,740 A | * | 4/2000 | Whitehead et al. .......... 700/57 |

FOREIGN PATENT DOCUMENTS

| | | | |
|---|---|---|---|
| JP | 406142077 | 5/1994 | ................. 128/653 |
| WO | WO88/04153 | 6/1988 | ................. 128/774 |

OTHER PUBLICATIONS

"Video comparator system for early detection of cutaneous malignant melanoma", Eric R. Craine and Brian L. Craine, SPIE vol. 1653/Image Capture Formatting, and Display (1992), 11 pages.

"Blink comparison techniques applied to medical images", Eric R. Craine and Brian L. Craine, SPIE vol. 1444 Image Capture, Formatting, and Display (1991), pp. 389–399.

* cited by examiner

Primary Examiner—Leo Boudreau
Assistant Examiner—Abolfazl Tabatabai
(74) Attorney, Agent, or Firm—Cahill, Sutton & Thomas P.L.C.

(57) ABSTRACT

New or growing skin lesions are identified by providing digital baseline image data of an area of a subject's skin, and storing the baseline image data. An imaging system is operated to produce up-to-date digital image data of the skin area directly from the subject or from a photograph thereof as a real time input to a computer. The stored baseline image data also is provided to the computer. The up-to-date image data and baseline image data are alternately displayed on a monitor in a blinking mode. The orientation, focus, and/or distance of the camera from the actual area or photograph thereof so as to frame, scale, and/or align features of the alternately displayed images. A frame of the aligned up-to-date image is digitized and stored. The stored up-to-date image data and the baseline image data are alternately displayed on a monitor in a blinking mode to visually identify lesions which blink enough to identify a new or significantly growing lesion.

9 Claims, 9 Drawing Sheets

Microfiche Appendix Included
(3 Microfiche, 201 Pages)

IMAGE COMPARATOR SYSTEM AND METHOD FOR DETECTING CHANGES IN SKIN LESIONS

REFERENCE TO MICROFICHE APPENDIX

A microfiche appendix (Appendix 1) containing a total of 3 sheets and 201 frames of microfiche is included in this application.

BACKGROUND OF THE INVENTION

The invention relates to a computer imaging system and method for detecting changing skin lesions and new skin lesions.

It is well known that rapid changes in the size of a mole or skin lesion may indicate the onset of precancerous or cancerous tissue growth and that early detection of such changes usually results in a much better prognosis for the patient, especially if the lesion is a melanoma. In the case of a melanoma, a delay of a month or two in detection may make the difference between successful treatment or death of the patient. Unfortunately, most people have difficulty detecting early changes in the size of a skin lesion because initial changes in size are slow and subtle. Furthermore, a physician observing a lesion usually does not have prior "baseline" or reference information on the lesion from which to judge the amount or rate of its growth.

Because there is no generally effective treatment for metastatic melanoma, even small cancers often prove fatal if not detected early. This is unfortunate, because few cancers provide a greater opportunity for early discovery and removal than melanoma, because cutaneous melanoma (1) is located on the skin surface where it is readily observed, and (2) usually undergoes an easily observable "radial growth" phase prior to metastasis.

The radial growth stage of a cancerous skin lesion therefore provides a window of opportunity during which the lesion can be detected and removed before metastasis, with a high probability of a complete cure.

The closest prior art is believed to be our publication "Video Comparator System for Early Detection of Cutaneous Malignant Melanoma", SPIE vol. 1653/Image Capture Formatting, and Display (1992). Various difficulties were encountered in providing a practical implementation of the basic technique described in that article using a microcomputer-based video imaging system for storing an image archive of historical reference images for each patient, registering and scaling current images with baseline images, and using a blink comparison of the image pairs in a manner that is readily acceptable by and useable by patients. Those difficulties led to the present invention.

There clearly is a great need, which up till now has not been fulfilled, for an inexpensive, workable, accurate system and technique by which ordinary people can conveniently monitor the growth of skin lesions on their entire bodies and submit such information to a dermatologist who can then expertly observe lesions which have significantly changed since a prior examination. Nor has there been any available, accurate system and technique which can be used even by scientists and doctors to correctly and accurately quantify and/or record the development of lesions over time and/or to record the response of lesions to various treatments, especially on a large number of subjects; there clearly is a great need for such a system and technique.

SUMMARY OF THE INVENTION

Accordingly, it is an object of the invention to provide an inexpensive, easily used system/method for detecting new skin lesions and/or skin lesions which have grown significantly.

It is another object of the invention to provide such a system for establishing a baseline record of image data of initial skin conditions and providing a meaningful comparison of later images of the same skin areas with the baseline images so as to readily and accurately identify all new lesions or pre-existing lesions which have significantly grown.

It is another object of the invention to provide such a system that allows patients to simply take photographs of their skin in the privacy of their homes and to use ordinary personal computers to identify new or significantly growing lesions on the basis of the information in such photographs.

It is another object of the invention to provide a quick, convenient way to align an image in good registration with another image, which may be of essentially the same subject matter, without introducing distortions in either image.

It is another object of the invention to provide a research tool to enable study and quantification of the natural history of skin lesions.

It is another object of the invention to provide a research tool to enable convenient study of the effects of various skin treatments on the human skin and lesions thereon.

Briefly described, and in accordance with one embodiment thereof, the invention provides a method of identifying new or growing skin lesions by providing digital baseline image data of an area of a subject's skin, and storing the baseline image data. An imaging system is operated to produce current digital image data of the skin area directly from the subject or from a photograph thereof as an input to a computer, and storing the baseline image data in the computer. The current image data and baseline image data are alternately displayed in an alternating display of selectable frequency on a monitor associated with the computer. The orientation, focus, and/or distance of the camera from the actual area or photograph thereof are adjusted so as to align images of two or more corresponding but separated features of the alternately displayed images. A frame of the aligned current image data is digitized and stored with the baseline image data. The stored aligned current image data and the baseline image data are alternatively displayed in a blinking (alternating) mode on a monitor to visually identify lesions which appear to flash on and off, or to pulsate, to thereby identify new and/or significantly growing/changing lesions. The subject then can have a dermatologist observe the identified lesions.

DETAILED DESCRIPTION OF THE PREFERRED EMBODIMENTS

Figure 1:
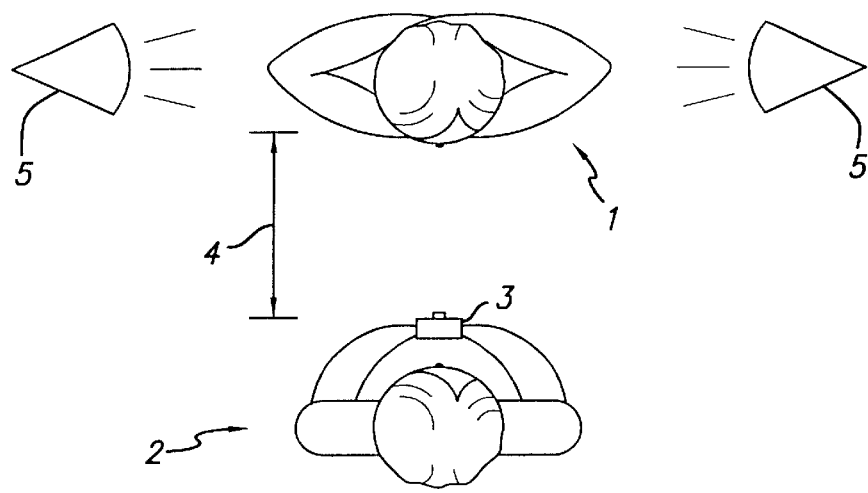
FIG. 1 is a top view diagram illustrating an initial step of photographing the skin of a patient.

An initial step in identifying new or significantly growing skin lesions is to obtain digital "baseline" image data for all skin areas of interest for a particular subject. At a later time, properly scaled and aligned up-to-date digital images of the same skin area can be obtained and compared to baseline images to identify new/changing lesions and/or measuring lesions which are changing, growing or diminishing significantly. FIG. 1 shows a setup which allows suitable photographs to be taken of the skin of a subject 1 in the privacy of his/her home. Subject 1 stands in front of a light-colored wall. Lamps 5 are placed to illuminate either side of subject 1. A photographer 2 operating an ordinary flash camera 3, which can be a commonly available disposable camera, positions camera 3 a predetermined distance 4, preferably about 3 feet, in front of the skin area to be photographed.

Figure 2A:
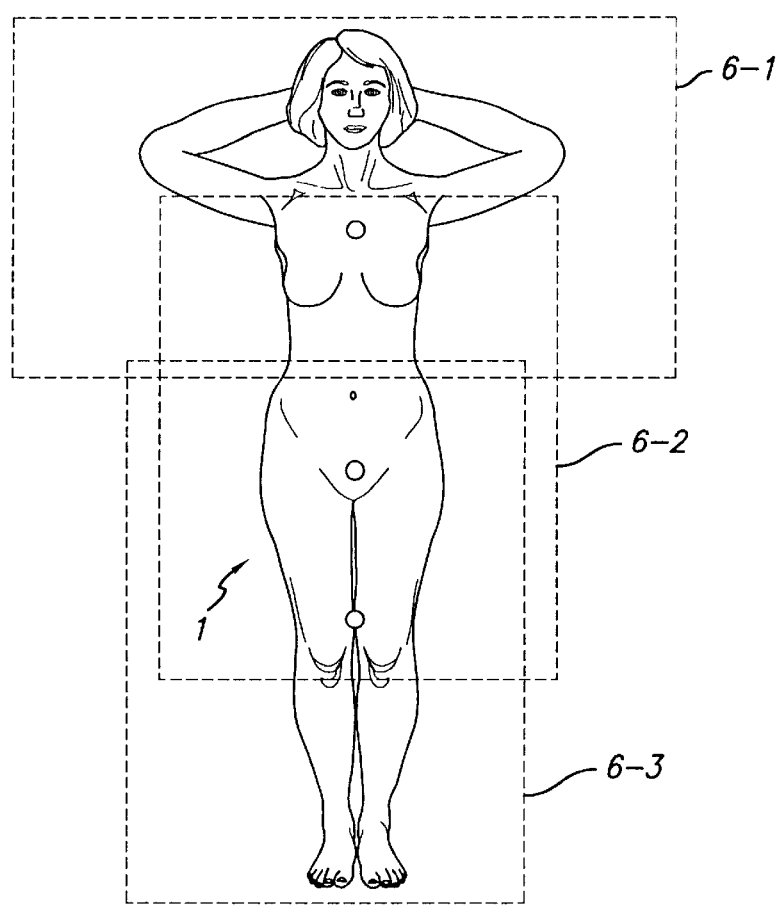
FIGS. 2A–2D are diagrams illustrating the field of view of each of twelve photographs taken with the setup of FIG. 1.
Figure 2B:
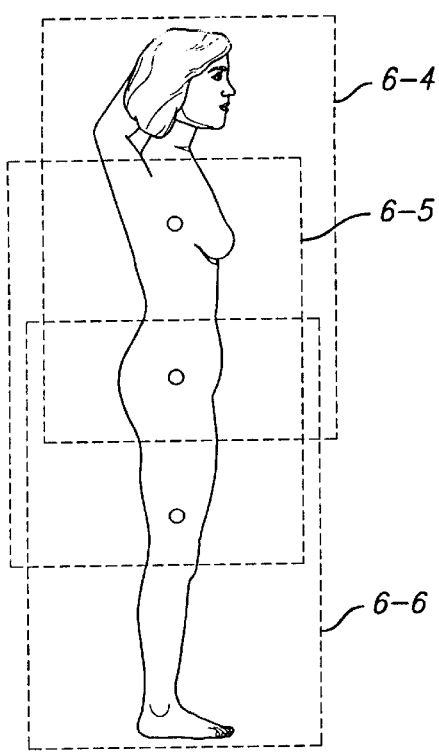
Figure 2C:
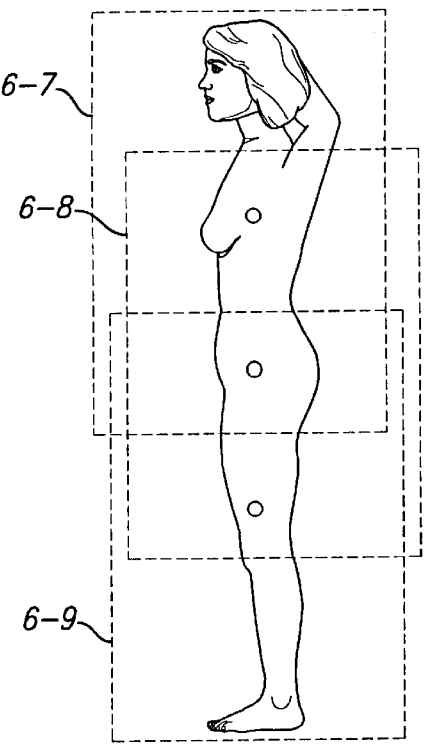
Figure 2D:
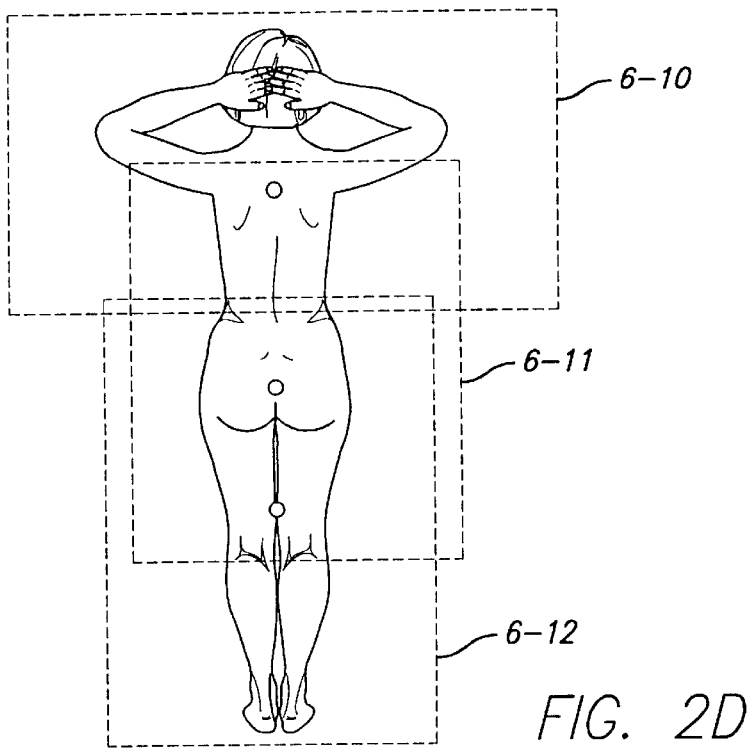

FIGS. 2A–2D illustrate a suitable protocol of "frames" or fields of view of subject 1 to be photographed. In FIG. 2A, the first frame is identified by numeral 6-1. Then, a second frame 6-2 is photographed, with considerable overlapping of frame 6-1. Similarly, a lower frame 6-3 considerably overlaps frame 6-2. The right side of the subject 1 is photographed to provide three overlapping frames 6-4, 6-5, and 6-6. FIG. 2C shows the left side of the subject, outlined by frames 6-7,8,9. Finally, the back side of subject 1 is photographed in overlapping frames 6-10,11,12.

The specific procedure for taking the photographs using the setup of FIG. 1 in the "protocol" of FIGS. 2A–D is described with reference to the flow chart of FIG. 4A, wherein the first step 20 is to arrange the space and lighting as indicated in FIG. 1. If the preferred or standard "image sets" indicated in FIGS. 2A–D are to be used, as indicated in decision block 21, and if the subject's entire body is to be imaged as indicated in decision block 23 and block 25, then the protocol of FIGS. 2A–2D is used. If only a portion of the subject's body is to be photographed, then a similar procedure is followed for that portion, as indicated by block 24. Blocks 26–33 identify the steps to be taken during each photo session of the subject, for obtaining photographs to establish a baseline or for taking subsequent up-to-date photographs for comparison with the baseline image data.

Figure 3:
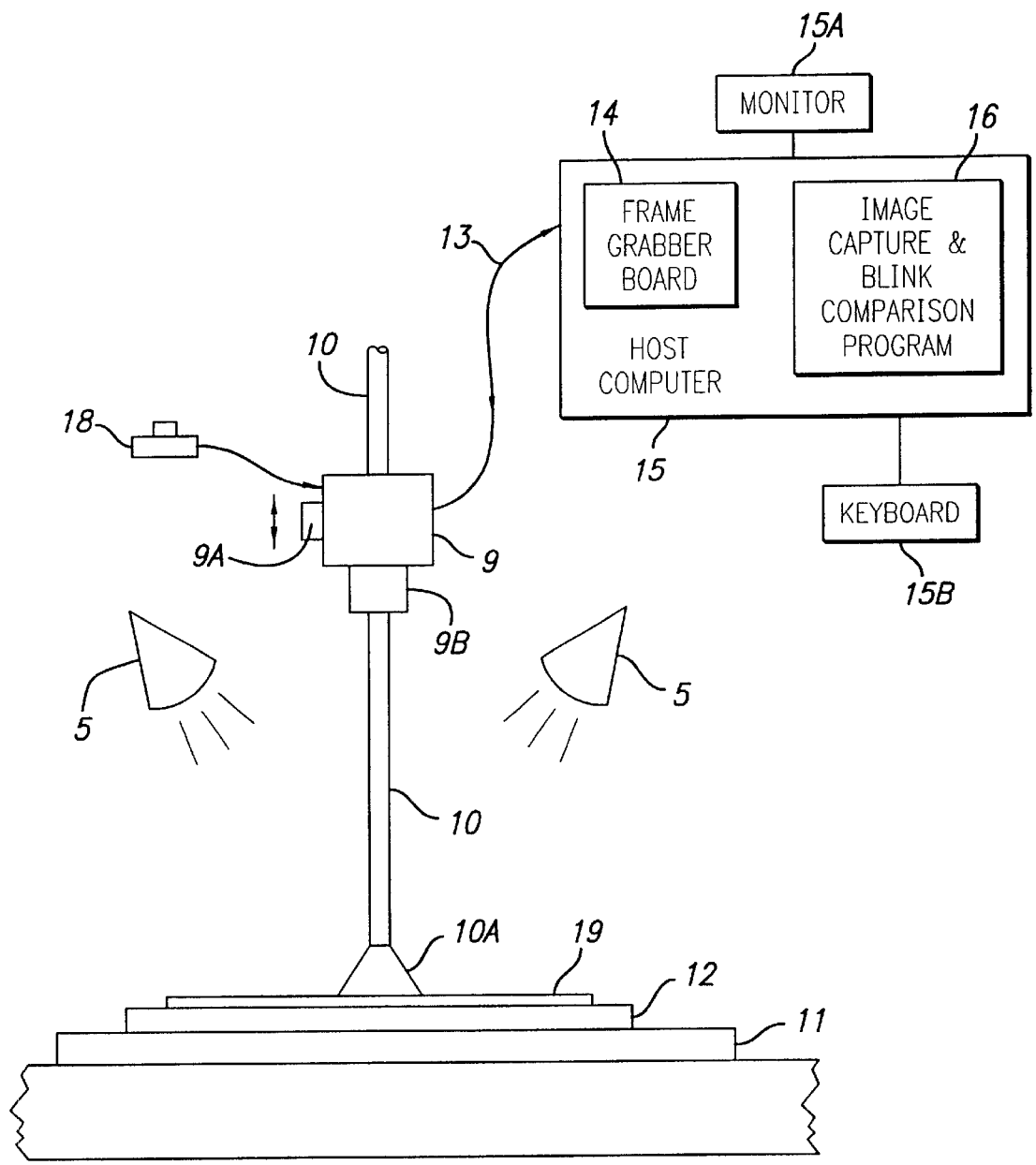
FIG. 3 is an elevation view diagram illustrating the apparatus used in digitizing the photographs of FIGS. 2A–D in accordance with the present invention.

After the above photographs have been taken, each with the camera 3 held in a vertical plane (so its optical axis is approximately horizontal) at an appropriate elevation corresponding to the frame (of FIGS. 2A–D) being photographed and at the same distance 4 (FIG. 1) from the skin area being photographed, the film or the disposable camera 3 can be sent to a center that arranges for proper development of the photographs and then uses the setup shown in FIG. 3 to digitize the photographs.

Referring to FIG. 3, a suitable CCD camera 9, such as a model XC-75 available from Sony Corporation, is mounted on a scaling and focusing rack that includes a vertical pole 10 and base 10A such that CCD camera 9 is supported directly over a stage 11. Stage 11 has a horizontal smooth surface on which a photo platform 12 is laterally moveable. Each developed photograph 19 obtained during the previously described procedure is placed, one at a time, on platform 12 in the proper sequence; such photographs can be approximately 6 inches square.

CCD camera 9 is connected by a suitable electrical cable 13 to a power supply and to a frame grabber board 14 that is plugged into a host computer 15. Computer 15 can be a PC (personal computer) such as a PC with a WINDOWS operating system and suitable image capture and comparison software 16. Microfiche Appendix 1 contains the listed instructions that constitute the software program in block 16.

Numeral 9A designates controls for adjusting the height of CCD camera 9 and focusing it and the focal length of its zoom 20 lens 9B on photograph 19. A trigger switch 18 connected to CCD camera 9 causes a present image captured by a CCD array of camera 9 to be sent to frame grabber board 14 when trigger switch 18 is actuated. The image capture software 16 (disclosed in microfiche Appendix 1) stores the digitized baseline image data of the area of photograph 19 presently imaged by camera 9 in a suitable file.

Lights 5 illuminate photograph 19.

Note that the twelve photographs framed as indicated by numerals 6-1,2 . . . 12 according to the protocol of FIGS. 2A–D during the above-described procedure were selected because an amateur photographer can easily provide these fields of view and thereby essentially eliminate the risk of missing an important skin area; the resolution of the image is adequate for accurate digitizing if the distance 4 (FIG. 3) is about 3 feet. It is important to try to get enough photographs by the amateur photographer to ensure that no skin area is missed, and the best way to ensure this is to obtain a large number of overlapping frame areas. Then, to provide adequate size images for the subsequently described alternating comparison of present image data with baseline image data, CCD camera 9 can be more expertly controlled to image and digitize suitable smaller subareas of large photographs 19. Typically, 40 to 45 such subareas will be digitized for a subject.

Figure 4A:
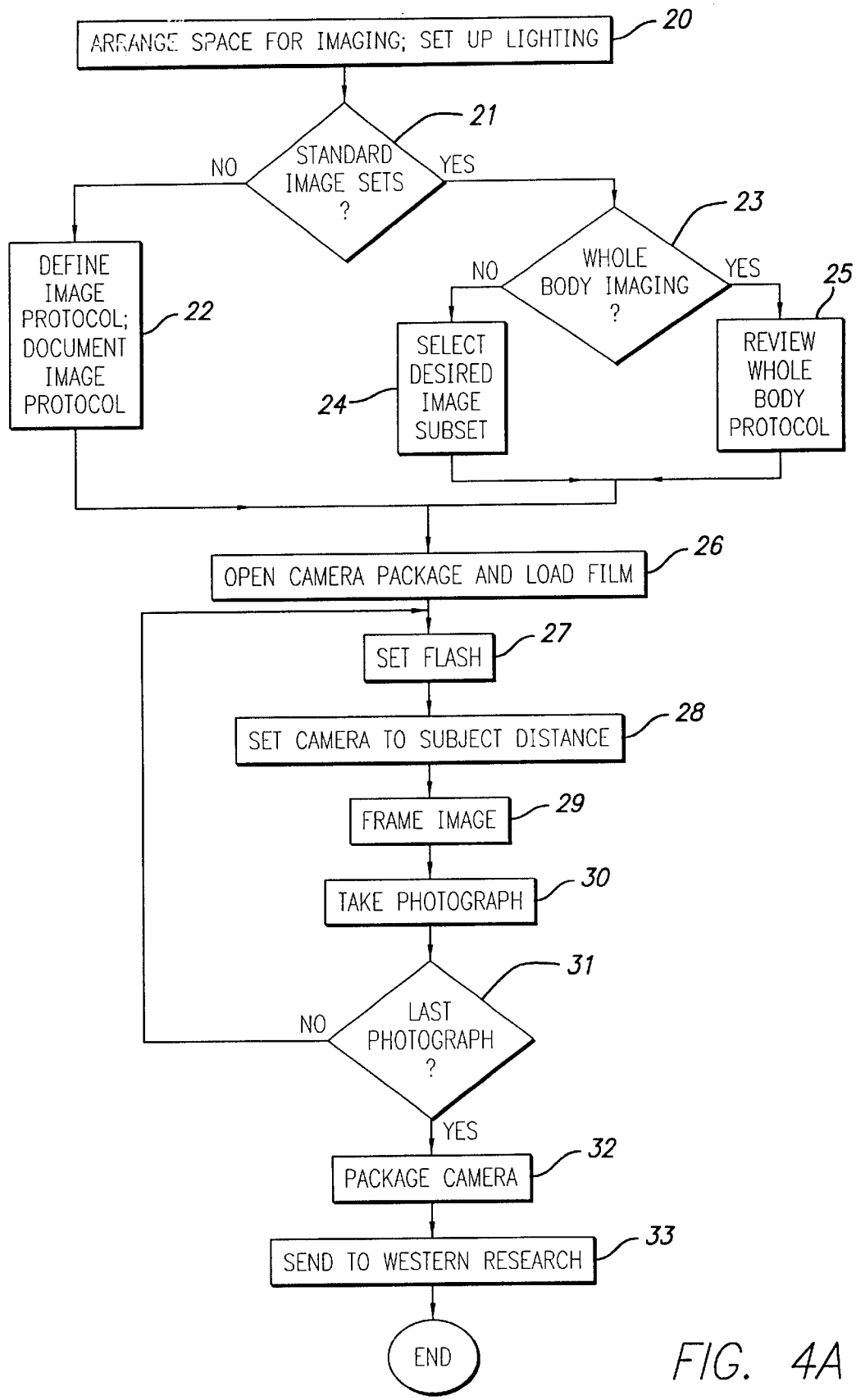
FIG. 4A is a flow chart useful in describing the procedure for taking the photographs of FIGS. 2A–2D using the setup of FIG. 1.
Figure 4B:
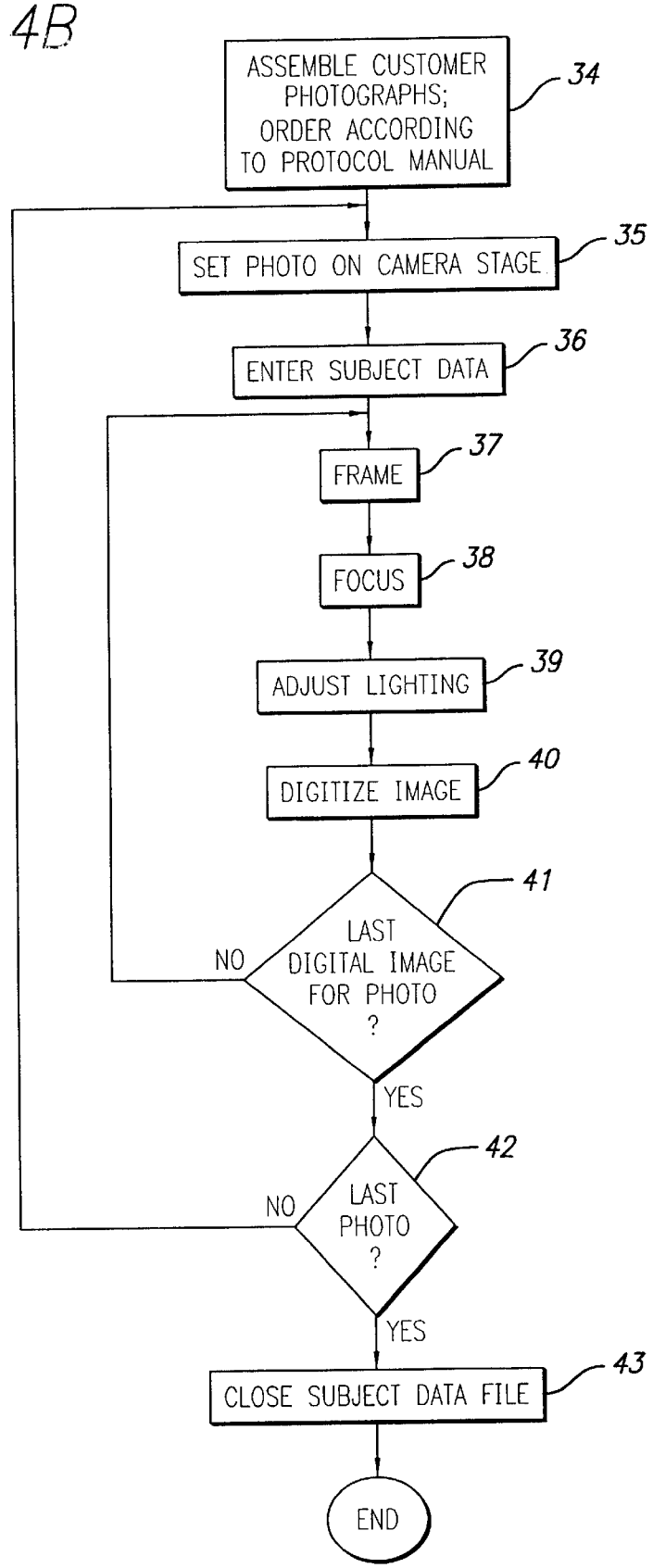
FIG. 4B is a flow chart useful in describing the technique for digitizing the photographs taken in accordance with FIG. 4A to establish digitized "baseline" image data for a particular patient.

The flow chart of FIG. 4B shows the protocol for making baseline digital images from the photographs framed as indicated by numerals 6-1,2 . . . 12 in FIGS. 2A–D. The procedure includes arranging the photographs in the same order as indicated in FIGS. 2A–D; see block 34 of FIG. 4B. The first photograph 19 then is placed on stage 12, as indicated by block 35. Host computer 15 includes a keyboard 15B by means of which data on subject 1 is entered, along with identification information identifying which of the twelve photographs 6-1,2 . . . 12 is now being digitized, which smaller subarea of that photograph is being digitized, and the portion of the subject's body to which that subarea corresponds. As indicated in block 37, the selected subarea of the present photograph 19 then is selected by viewing the image on monitor 15A of host computer 15 which shows the present image received by the CCD array of camera 9.

As indicated in block 38, the operator then focuses the lens of camera 9. As indicated in block 39, the operator then adjusts the lighting and the contrast controls if desired. (Lighting can be adjusted by f-stop adjustment of the camera lens; contrast can also be adjusted in the computer display software.) As indicated in block, 40, the next step is to actuate switch 18 to cause frame grabber 14 to digitize the image. If more subareas of the present photograph 19 are to be digitized, the procedure of blocks 37–40 is repeated, as indicated by decision block 41. When all desired subareas of photograph 19 have been digitized, it is removed from platform 12 and the next photograph 19 is placed thereon.

The foregoing procedure is repeated, until all of the photographs 19 have been digitized as desired. The digitized image data then is stored in a suitable baseline file (e.g., in a hard disk drive in computer 15) in the desired order and with the desired identification and information appended.

Figure 4C:
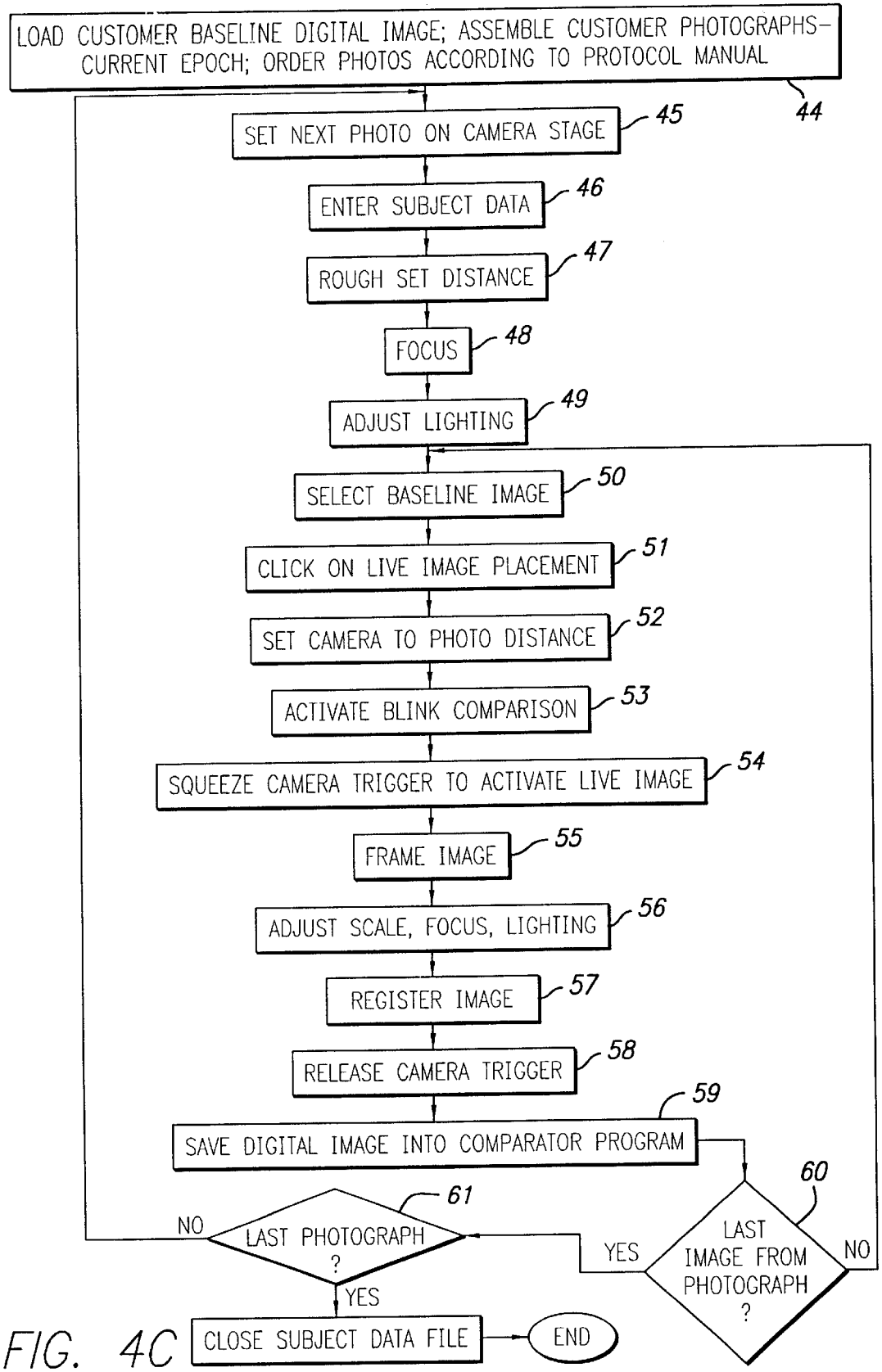
FIG. 4C is a flow chart useful in describing the technique for using information from a current set of photographs of the patient to provide an accurate blink comparison of present skin images with corresponding digitized baseline images obtained in accordance with FIG. 4B.

Any time after the baseline image data has been stored, the above procedure of FIG. 4A can be repeated to obtain and develop an up-to-date set of photographs of the subject's skin. As indicated in block 44 of FIG. 4C, the patient's baseline image information then is loaded into computer 15 and the up-to-date photos are arranged in order. The equipment of FIG. 3 then is used to digitize the up-to-date photographs. The first up-to-date photograph 14, framed as indicated by numeral 6-1 in FIG. 2A, is set on platform 12, and identifying information is entered via a keyboard as indicated in blocks 45 and 46. CCD camera 9 is preset to approximately the correct distance above platform 12, as indicated in block 47.

After suitable focusing (block 48) and light adjustments (block 49), host computer 15 is instructed to call up the previously stored baseline image data of a desired portion of the subject's skin, as indicated in block 50. Then, as indicated in block 51, computer 15 is instructed to display the "live" image of the portion of the current photograph within its present field of view. As indicated in block 52, the operator then sets the camera height so that the "live" image is approximately the same size as the previously displayed baseline image. As indicated in blocks 53 and 54, the operator then instructs the computer to alternately display the baseline image and the "live" image on the monitor to allow a "blink" comparison thereof The operator then observes features of the alternately displayed baseline image and "live" image, and adjusts the orientation, scale, focus, lighting, and image contrast as necessary to ensure that the "live" or current image is aligned as precisely as possible, and photometrically matches as best possible, with the alternately displayed baseline image, as indicated in blocks 55, 56, and 57. That is, the live image should be not only mechanically aligned with the displayed baseline image, but the two images should also have about the same level of "darkness" or "lightness".

When this is accomplished, the camera trigger 18 is released (block 58), which causes the properly aligned and scaled live image (which is acquired by squeezing the camera trigger 18) of the selected portion of the photograph on platform 12 to be digitized and stored with the corresponding baseline image, so the two may be stored as a pair in the same directory. Microfiche Appendix 1 includes object code of the comparison program in block 16 of FIG. 3 which effectuates the above described blink comparison and storage (block 59) of the matched pair of images constituting the baseline image and the current image of the same skin area. As indicated in blocks 60 and 61, the foregoing procedure is repeated for each subarea of the first up-to-date photograph 6-1 and then is repeated again for each subarea of each of the other up-to-date photographs.

The above described procedure provides baseline images of all areas of interest of the subject's skin and corresponding later "up-to-date" images by using photographs taken in the privacy of the subject's home. However, in accordance with the invention, it also is possible to use CCD camera 9 to accomplish "direct digital imaging" of the baseline images and subsequent "up-to-date" images of the subject's skin instead of photographing the subject's body as described above.

Figure 5:
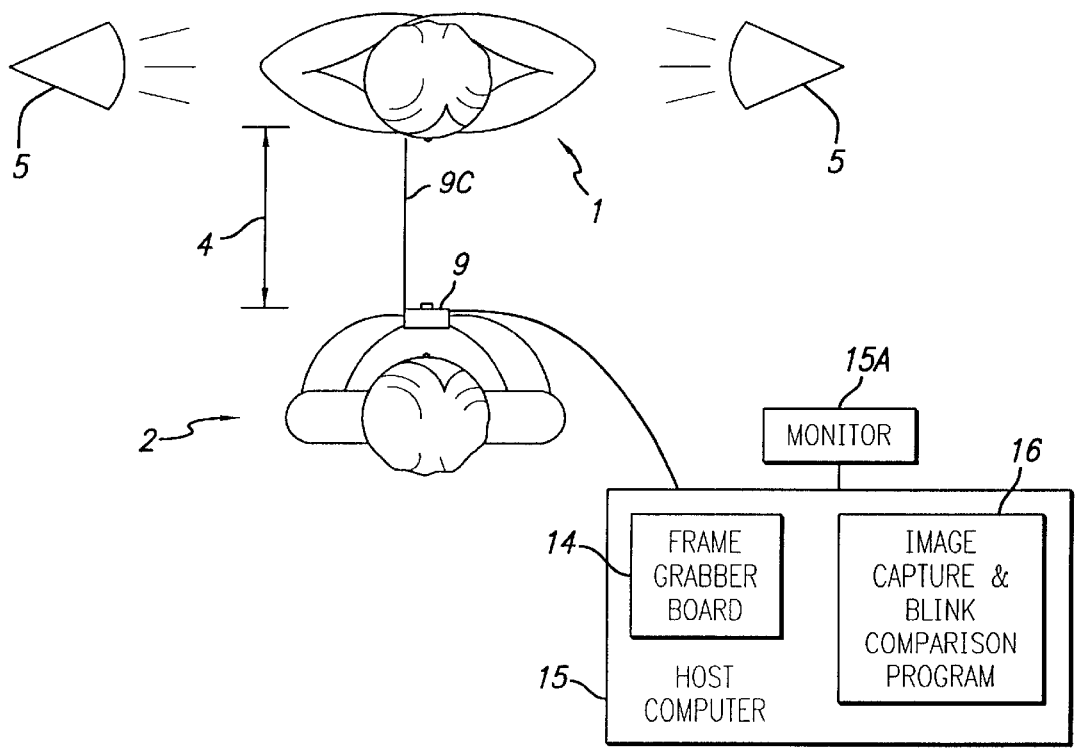
FIG. 5 is a top plan view of a setup for direct digital imaging of the skin of a patient and digitizing images.

FIG. 5 shows a suitable arrangement for such direct digital imaging, wherein lamps 5 illuminate the subject 1. Photographer 2 holds a CCD camera 9 on a pistol grip having a control switch. An adjustable rod 9C is attached to the pistol grip to ensure that approximately the proper distance between the lens of the CCD camera 9 and the skin area of interest is maintained when the tip of rod 9C touches the skin area to be imaged. CCD camera 9 is connected by cable 13 to frame grabber card 14 in host computer 15, as previously described.

Figure 6A:
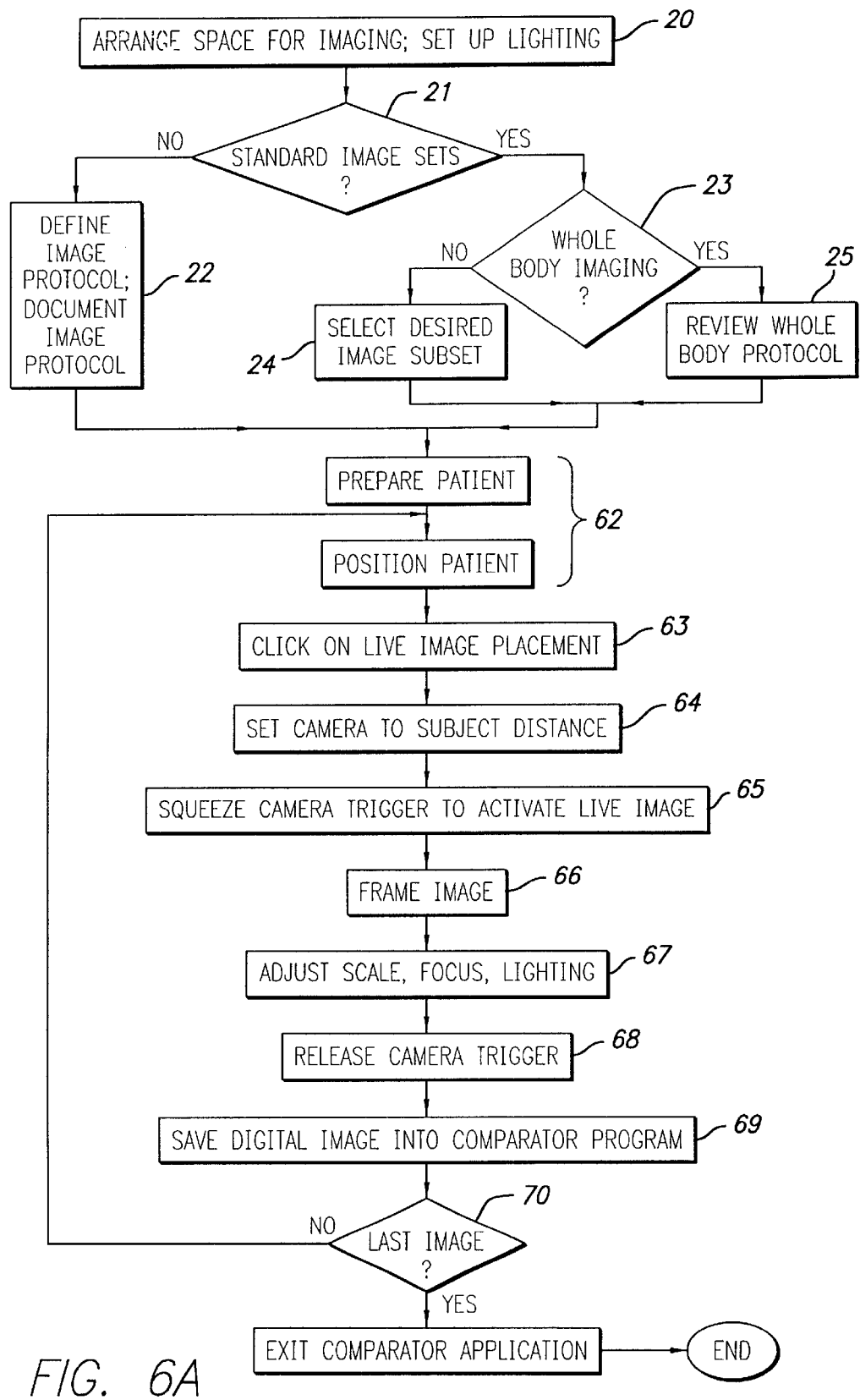
FIG. 6A is a flow chart useful in describing the technique for making baseline images using the direct digital imaging setup of FIG. 5.

The flow chart of FIG. 6A indicates how the arrangement of FIG. 5 also can be utilized to provide baseline images by "direct digital imaging" of the subject 1. The procedure of blocks 20–25 may be as previously described with reference to the flow chart of FIG. 4A. As indicated in block 62 the subject 1 is prepared and positioned according to FIG. 2A. As indicated in block 63, computer 15 is instructed by using a conventional mouse to click on an icon indicating that a "live" image of subject 1 is to be "framed", aligned and scaled as necessary, and digitized. CCD camera 9 is set to a suitable distance by touching the tip of rod 9C to the skin area of interest on subject 1, as indicated in block 64. The control switch on a pistol grip (not shown) on which CCD camera 9 is mounted is actuated to cause a live image to be transmitted to frame grabber 14, digitized and displayed on the monitor 15A of computer 15, as indicated in block 65.

The operator aims CCD camera 9 to "frame" the desired field of view, as indicated in block 66. As indicated in block 67, the scale, focus, and lighting are adjusted as necessary to produce the desired monitor image of the skin area within the field of view of CCD camera 9. The trigger switch of CCD camera 9 is released, which causes the displayed digital image to be loaded into the comparison program file 16 in computer 15, as indicated in block 68 and 69. As indicated in decision block 70, the above procedure then is repeated for all areas of interest on the skin of subject 1.

This alternative method of obtaining baseline image data is much faster than the technique of taking and developing photographs, and is advantageous for use in a clinic, if the subject is willing to forgo privacy of his/her home for the procedure.

Figure 6B:
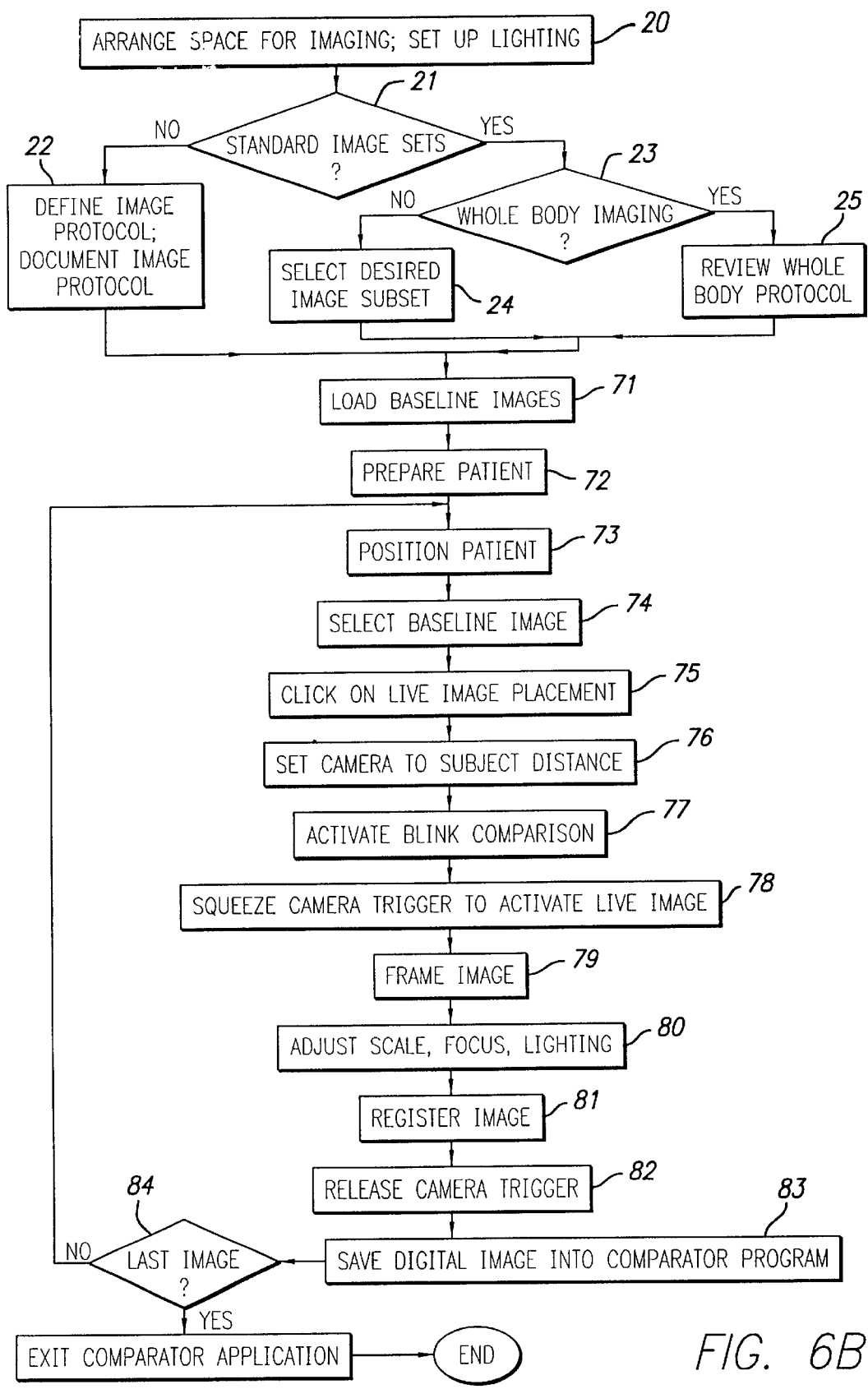
FIG. 6B is a flow chart useful in describing the technique for using the direct digital imaging setup of FIG. 5 to compare present skin image information with corresponding stored baseline image information to identify new or significantly growing skin lesions.

The flow chart of FIG. 6B indicates how "up-to-date" images, i.e., "current" images of the subject's skin can be obtained by direct digital imaging, regardless of how the subject's baseline image data was obtained and stored. The setup of FIG. 5 is used for such direct digital imaging. The procedure of blocks 20–25 of FIG. 6B is identical to that described above with reference to FIG. 4A. The subject's baseline data is loaded into computer 15, as indicated by block 71. After the subject 1 is prepared and positioned (block 73), the patient is suitably positioned to "frame" the skin areas of interest in the field of view of CCD camera 9, as indicated in block 73. A corresponding baseline image is selected, as indicated in block 74, and displayed on the monitor of computer 16, as indicated by block 75. CCD camera 9 is positioned directly in front of the skin area of interest at the distance determined by rod 9B, as indicated by block 76.

The above mentioned blink comparison algorithm is activated, as indicated by block 77, and the above mentioned trigger switch is squeezed to display the image within the field of view of CCD camera 9 on the monitor of computer 15, as indicated by block 78. The operator adjusts CCD camera 9 to adjust the scale, focus, lighting, and orientation of CCD camera 9 to bring into alignment two or more corresponding but separate features of the alternately displayed baseline image and the current live image on the monitor, as indicated in blocks 79 and 80. When proper alignment is achieved, the image is registered, as indicated by block 81. As indicated in block 82, the trigger switch of the pistol grip of CCD camera 9 is released, causing the aligned, registered current image data to be loaded into the comparison program with the corresponding baseline image data as indicated in block 83. Then, as indicated by block 84, the foregoing procedure is repeated for every area of interest of the subject.

Figure 7:
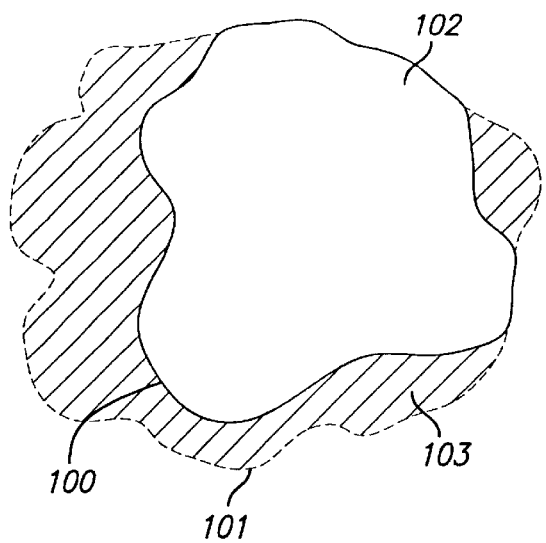
FIG. 7 is a diagram of a baseline image of a skin lesion superimposed on a present image of the same lesion.

Referring to FIG. 7, numeral 100 indicates the outline of the baseline image data of a typical lesion. Numeral 101 indicates the outline of an up-to-date or current image of the same lesion, typically obtained a few months to a few years later. In the example of FIG. 7, the up-to-date lesion image 101 is larger than the baseline image 100. The cross hatched area 103 indicates the areas in which the lesion has grown since the baseline image 100 was obtained.

We have learned that the above described technique for scaling and aligning the up-to-date or current images of the subject with his/her corresponding baseline images using the blink comparison technique results in very accurate evaluation of which lesions have newly appeared and which ones have grown significantly relative to the corresponding baseline images. Even though alignment and scaling between alternately displayed or blinking baseline images and corresponding up-to-date images is never perfect, the "blinking" is slight for those lesions which have not significantly grown. However, if a new lesion appears, or if there has been substantial growth of a preexisting lesion, the blinking, which corresponds to a change in size between the outline 100 and the outline 101 in FIG. 7, is quite dramatic and easily interpreted to indicate which lesions should be promptly observed by a dermatologist. This technique has been shown to be far superior in detecting new or changed lesions than presently accepted competing techniques of skin self-examination in mirrors or side-by-side comparison of photographic images.

By way of definition, the term "blink" is intended to refer to either the process of alternately displaying approximately registered images that differ in size and/or shape or to the phenomenon whereby features of the alternately displayed images are sufficiently different that they identify a significant change in one of the lesions or presence of a new lesion. That is, the term means the alternate displaying of the lesions or features to cause them to appear to flash or pulsate so as to indicate that the lesions or features vary in size, shape, or presence enough to identify a significantly growing (or shrinking) lesion or the presence of a new lesion feature.

Also by way of definition, the term "current image" or "current image data" is intended to refer to any corresponding image or image data obtained after the baseline image.

While the invention has been described with reference to several particular embodiments thereof, those skilled in the art will be able to make the various modifications to the described embodiments of the invention without departing from the true spirit and scope of the invention. It is intended that all elements or steps which are insubstantially different or perform substantially the same function in substantially the same way to achieve the same result as what is claimed are within the scope of the invention.

For example, the images could be registered using software to adjust or "distort" the locations of various pixels of one image to align it with corresponding pixels of the other image. (However, this technique can produce unacceptable distortion within the lesion image itself, thus rendering detection of change of the lesion much less reliable.)

As another example, instead of alternately displaying current and baseline images to visually detect significant changes, one image could be mathematically subtracted from the other. However, the registration between the baseline and present image must be very precise for the subtraction technique to work well. Or, the present image could be added, along with a bit of offset, to the baseline image so that all of the lesions appear double. It should then be possible in some cases to view the resulting pairs of images and identify significantly changed lesions. Furthermore, the images could be projected on a screen instead of using a monitor.

Another possible alternative to the above described method and apparatus using digital image data is to utilize analog video images. For example, baseline imagery of a person's skin could be recorded on video tape. Later a video camera could be utilized to provide a current live image of the person's skin. Both a video playback of the baseline images from the video tape and the video signal representing the current live image of the same area of the person's skin could be input to a conventional video switcher (such as a Kramer Model VM-33Z) that operates to alternately select the baseline video playback images and the current video live images being input to the video monitor.

Then, using exactly the same procedure described above for use of digital image data, an operator views the alternately blinking images on the monitor and adjusts the video camera to align, focus, and scale the current video live images to the video playback baseline images until the alternately blinking images match sufficiently. When the current live images and the baseline images are sufficiently registered and scaled, the video camera can then record the live images on video tape. Then playback of the recorded live images can be input to a video switcher along with the playback of the baseline images. The output of the video switcher then is input to a monitor or other suitable display. The resulting alternately blinking images then can be viewed to identify new or significantly changed lesions. Or, the output of the video switcher alternately displaying current live images and pre-recorded baseline images can be recorded on tape. The resulting tape showing alternately blinking baseline images and registered, scaled current live images then can be viewed to identify new or significantly changed lesions.

What is claimed is:

1. A method of obtaining an approximate alignment of a current image of a portion of person's skin with a prior baseline image of the same portion of the person's skin sufficient to allow accurate identification of significant changes in any of a plurality of lesions on the portion of the person's skin by repetitively, alternately displaying the current image and the prior baseline image, the method comprising:

(a) providing baseline image data of the portion of the person's skin;

(b) substantially later than step (a), operating an imaging system including a camera to produce current digital image data of the portion of the person's skin directly from the portion of the person's skin or from a photograph thereof as an input to a processor;

(c) providing the baseline image data as an input to the processor;

(d) repetitively, alternately displaying a current image representative of the current image data and a baseline image representative of the baseline image data on a monitor associated with the processor; and (e) simultaneously with step (d), mechanically aligning the current image with the baseline image by adjusting the orientation, focus, and/or distance of the camera from the portion of the person's skin or photograph thereof so as to provide a best fit approximate alignment of the repetitively, alternately displayed current image with the repetitively, alternately displayed baseline image.

2. The method of claim 1 wherein any changes in shape of any of the lesions caused by changes in shape of tissue supporting the lesions are medically insignificant.

3. The method of claim 1 including repetitively, alternately displaying the approximately aligned current image and the baseline image on the monitor to allow visual identification of any lesion which appears to blink enough to identify it as a new lesion or a significantly changed lesion.

4. The method of claim 1 wherein step (e) includes digitizing and storing a frame of the approximately aligned current image, and wherein the method further includes repetitively, alternately displaying the approximately aligned, digitized and stored current image and the baseline image on the monitor to allow visual identification of any lesion which appears to blink enough to identify it as a new lesion or a significantly changed lesion.

5. The method of claim 1 wherein step (a) includes i. operating another camera to take a plurality of substantially overlapping photographs of the person's skin to ensure an entire desired area thereof is photographed, and developing the photographs;

ii. operating the imaging system to produce first digital image data from one of the photographs;

iii. repeating step (ii) to produce additional digital image data from various ones of the photographs as necessary to provide the digital baseline image data by combining the first digital image data and the additional image data; and iv. storing the digital baseline image data.

6. A system for obtaining an approximate alignment of a current image of a portion of person's skin with a prior baseline image of the same portion of the person's skin sufficient to allow accurate identification of significant changes in any of a plurality of lesions on the portion of the person's skin by repetitively, alternately displaying the current image and the prior baseline image, the system comprising:

(a) means for providing baseline image data of the portion of the person's skin;

(b) means for operating an imaging system including a camera to produce current digital image data of the portion of the person's skin directly from the portion or from a photograph thereof as an input to a processor;

(c) means for providing the baseline image data as an input to the processor;

(d) means for repetitively, alternately displaying a current image representative of the current image data and a baseline image representative of the baseline image data on a monitor associated with the processor; and (e) image alignment means for adjusting the orientation, focus, and/or distance of the camera from the portion of the person's skin or photograph thereof so as to provide a best fit approximate alignment of the repetitively, alternately displayed current image with the repetitively, alternately displayed baseline image.

7. The system of claim 6 including means for repetitively, alternately displaying the approximately aligned current image and the baseline image on the monitor to allow visual identification of any lesion which appears to blink enough to identify it as a new lesion or a significantly changed lesion.

8. The system of claim 6 including means for digitizing and storing a frame of the aligned current image, the method further including repetitively, alternately displaying the best fit aligned, digitized and stored current image data and the baseline image on the monitor to allow visual identification of any lesion which appears to blink enough to identify it as a new or significantly changed lesion.

9. A system for obtaining an approximate alignment of a current image of a portion of person's skin with a prior baseline image of the same portion of the person's skin sufficient to allow accurate identification of significant changes in any of a plurality of lesions on the portion of the person's skin by repetitively, alternately displaying the current image and the prior baseline image, the system comprising:

(a) a memory for storing digital baseline image data of an area of the person's skin and providing the baseline image data as an input to the processor;

(b) an imaging system including a camera to produce current digital image data of the portion of the person's skin directly from the portion or from a photograph thereof as an input to a processor;

(c) a stored program executable by the processor for repetitively, alternately displaying a current image representative of the current image data and a baseline image representative of the baseline image data on a monitor associated with the processor;

(d) image alignment apparatus for adjusting the orientation, focus, and/or distance of the camera from the portion of the person's skin or photograph thereof so as to provide a best fit approximate alignment of the repetitively, alternately displayed current image with the repetitively, alternately displayed baseline image; and (e) a digitizing apparatus coupled to the processor for digitizing a frame of the aligned current image and storing it, the repetitive, alternate displaying of the aligned and stored current image and the baseline image on the monitor allowing visual identification of any lesion which appears to blink enough to identify it as a new lesion or a significantly changed lesion.

* * * * *